United States Patent [19]

Nickisch et al.

[11] Patent Number: 4,500,522
[45] Date of Patent: Feb. 19, 1985

[54] 7α-ACYLTHIO-15,16-METHYLENE-3-OXO-17α-PREGNA-1,4-DIENE-21,17-CARBOLACTONES, THEIR PREPARATION AND USE AS MEDICINAL AGENTS

[75] Inventors: Klaus Nickisch; Dieter Bittler; Henry Laurent; Rudolf Wiechert; Wolfgang Losert, all of Berlin, Fed. Rep. of Germany

[73] Assignee: Schering Aktiengesellschaft, Berlin and Bergkamen, Fed. Rep. of Germany

[21] Appl. No.: 516,391

[22] Filed: Jul. 22, 1983

[30] Foreign Application Priority Data

Jul. 22, 1982 [DE] Fed. Rep. of Germany ....... 3227598

[51] Int. Cl.$^3$ ............................................. A61K 31/58
[52] U.S. Cl. .................................. 514/173; 260/239.57
[58] Field of Search ..................... 260/239.57; 424/241

[56] References Cited

U.S. PATENT DOCUMENTS

| | | | |
|---|---|---|---|
| 3,763,147 | 10/1973 | Arth | 260/239.57 |
| 3,890,304 | 6/1975 | Weier | 260/239.57 |
| 4,129,564 | 12/1970 | Weichert et al. | 260/239.57 |
| 4,291,029 | 9/1981 | Weichert et al. | 260/239.57 |

*Primary Examiner*—Elbert L. Roberts
*Attorney, Agent, or Firm*—Millen & White

[57] ABSTRACT

7α-acylthio-15,16-methylene-3-oxo-17α-pregna-1,4-diene-21,17-carbolactones of the formula

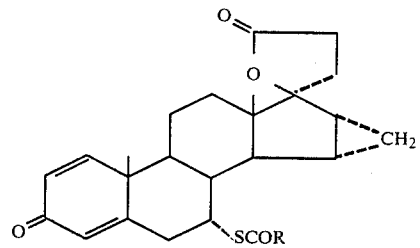

wherein
the 15,16-methylene group can be in the α- or β-configuration, and
R is a lower alkyl residue,
have altialdosterone activity.

They are prepared from corresponding Δ$^4$-unsaturated compounds by chemical or microbiological 1,2-dehydrogenation.

12 Claims, No Drawings

7α-ACYLTHIO-15,16-METHYLENE-3-OXO-17α-PREGNA-1,4-DIENE-21,17-CARBOLACTONES, THEIR PREPARATION AND USE AS MEDICINAL AGENTS

BACKGROUND OF THE INVENTION

The present invention relates to new steroidal compounds which have valuable pharmacological properties.

For the treatment of certain forms of hypertonia, of edemas, of primary aldosteronism, and of other endocrinological imbalances caused by aldosterone, and for use as diuretics, compounds are employed which reverse the effect of aldosterone or deoxycorticosterone on the excretion of sodium and potassium salts. These include as their most well-known representative the compound spironolactone, which has been available commercially for some time. However, undesirable endocrinic side effects frequently occur in the treatment with spironolactone. These are evoked by the antiandrogenic and progestational activity of spironolactone. Thus, with a relatively long-term treatment of male patients with spironolactone, occurrence of gynecomastia is observed (Smith, W. G., The Lancet, 1962, p. 886; Mann, N. M., JAMA 1963, p. 778; Clark, E., JAMA 1965, p. 157; Greenblatt, D. J., JAMA 1973, p. 82) and impotence is observed as well (Greenblatt, D. J., JAMA 1973, p. 82), due to the antiandrogenic side effect of this active agent (Steelman, S. L. et al., Steroids 1963, p. 449; Schane, H. P., J. of Clinical Endocrinology and metabolism 1978, p. 691).

In contrast, the progestational side effects of spironolactone are blamed for secondary symptoms such as amenorrhea and cycle irregularities, in women treated with spironolactone. Both side effects can be confirmed in animal experiments as well as in vitro by the receptor binding test with the androgen and progestogen receptor, respectively.

SUMMARY OF THE INVENTION

It is an object of the present invention to make available compounds which are not only essentially equivalent or superior to spironolactone in antialdosterone effect, but exhibit greatly diminished antiandrogenic and progestational side effects.

Upon further study of the specification and appended claims, further objects and advantages of this invention will become apparent to those skilled in the art.

These objects have been attained by this invention by providing novel 7α-acylthio-15,16-methylene-3-oxo-17α-pregna-1,4-diene-21,17-carbolactones of Formula I

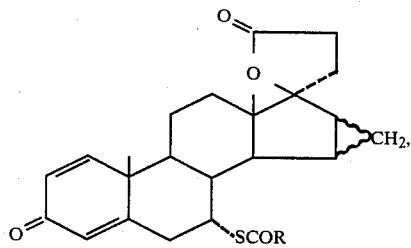

wherein the methylene group in the 15,16-position can be in the α- or β-configuration, and
R is lower alkyl.

DETAILED DISCUSSION

Suitable lower alkyl residues R of the 7α-positioned acylthio group are derived, e.g., from thiocarboxylic acids of up to 5 carbon atoms, such as thioacetic acid, thiopropionic acid, thiobutyric acid, and thiovaleric acid.

The antialdosterone activity was determined and measured in a test model by Hollmann, G. Hollmann et al., "Tubulaere Wirkungen und renale Elimination von Spironolactonen" [Tubular Effects and Renal Elimination of Spironolactones], Naunyn-Schmiedebergs Arch. Exp. Path. Pharmak. 247: 419 [1964]; P. Marx, "Renale Wirkungen des d-Aldosterons und seines Antagonisten Spironolacton" [Renal Effects of d-Aldosterone and Its Antagonist Spironolactone], Diss. Med. Fak. FU Berlin, 1966, all of whose disclosures are incorporated by reference herein.

ANDROGEN RECEPTOR BINDING TEST

The androgen receptor (protein) contained in the cytosol of a homogenate of rat prostates binds dihydrotestosterone (DHT) with high affinity but low capacity. If this receptor is loaded with $^3$H-DHT in the presence of the compound to be tested, then the extent to which $^3$H—DHT is displaced from the receptor depends on the concentration and binding affinity of the compound to be tested. After separation of the receptor-bound DHT from the unbound DHT, the binding can be determined in percent, and this value is plotted against the logarithm of the molar concentration of the test compound. The concentration of the test compound is now determined which is required for entirely displacing the reference compound from the receptor. The competition factor (CF) as a measure for the binding strength is defined as the ratio of concentration of test compound to the concentration of reference compound, so that a high CF value indicates low binding strength, but a low CF value indicates high affinity.

The progestogen receptor binding test takes place in the same way with the use of cytosol from rat uterus homogenate.

Antiandrogenic activity is found in compounds which, although themselves lacking androgenic activity, due to their high binding affinity, displace the body's own androgen from the receptor entirely or partially. This is observed to a certain extent with spironolactone. For this reason, a high competition factor is desirable in the androgen and progestogen receptor test.

Table 1 is a compilation of the relative values of antialdosterone efficacy (with spironolactone=1) and of the competition factors in the androgen receptor test ($C_A$) and in the progestogen receptor test ($C_G$) of spironolactone and of the compounds according to this invention, using as indicative examples 7α-acetylthio-15β,16β-methylene-3-oxo-17α-pregna-1,4-diene-21,17-carbolactone (B) and 7α-acetylthio-15α,16α-methylene-3-oxo-17α-pregna-1,4-diene-21,17-carbolactone (C):

| Compound | Relative Anti-aldosterone Activity | Competition Factor | |
| --- | --- | --- | --- |
| | | $C_A$ | $C_G$ |
| Spirono- | 1 | 8.9 | 21 |

-continued

| Compound | Relative Anti-aldosterone Activity | Competition Factor | |
|---|---|---|---|
| | | $C_A$ | $C_G$ |
| lactone | | | |
| B | 2 | 103 | 33 |
| C | 1.5 | 95 | 76 |

As the table shows, the compounds of this invention, in spite of a greatly reduced binding to progestogen and androgen receptors, are surprisingly superior to spironolactone with respect to their antialdosterone activity.

Thus, this invention furthermore relates to medicinal agents having antialdosterone activity containing a compound of Formula I. These pharmacologically effective compounds of Formula I can be utilized by conventional methods of galenic pharmacy for preparing medicines, especially those for oral administration. These compounds can be used in mammals including humans for the purposes which spironolactone is used, e.g., for the purposes mentioned above.

The dosage of the compound of this invention or of a mixture of several of these compounds of Formula I is, in human patients, 20–500 mg/day in total amount of active agent for the above-mentioned treatments. Unit dosages will be provided accordingly, e.g., 10–100 mg. Administration will be analogous to that of the conventional agent, spironolactone.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixer or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol, e.g., those described above.

This invention furthermore relates to a process for the preparation of 7α-acylthio-15,16-methylene-3-oxo-17α-pregna-1,4-diene-21,17-carbolactones of Formula I

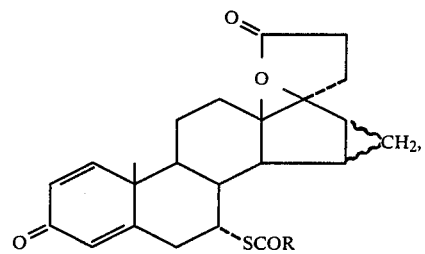

wherein
the 15,16-positioned methylene group can be in the α- or β-configuration, and
R is a lower alkyl residue,
comprising conventionally introducing a $\Delta^1$-double bond into a compound of Formula II

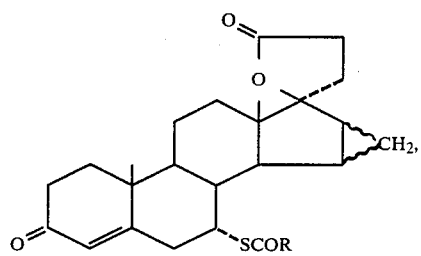

wherein
the 15,16-methylene group can be in the α- or β-configuration, and
R is a lower alkyl residue.

The $\Delta^1$-double bond can be introduced according to methods known per se and this step can be effected by chemical or microbiological processes. Suitable chemical dehydrogenation agents for the 1,2-dehydrogenation include, for example, selenium dioxide, 2,3-dichloro-5,6-dicyanobenzoquinone, chloranil, thallium triacetate, or lead tetraacetate.

Suitable microorganisms for 1,2-dehydrogenation include, for example, Schizomycetes, especially those of the genera Arthrobacter, e.g., simplex ATCC 6946; Bacillus, e.g., B. lentus ATCC 13805 and B. sphaericus ATCC 7055; Pseudomonas, e.g., P. aeruginosa IFO 3505; Flavobacterium, e.g., F. flavescens IFO 3058; Lactobacillus, e.g., L. brevis IFO 3354; and Nocardia, e.g., N. opaca ATCC 4276.

Preferably, the 1,2-dehydrogenation is carried out chemically. For this purpose, the 1,2-dihydro steroid can be heated in a suitable solvent with the dehydrogenation agent for a relatively long period of time. Suitable solvents include, for example, dioxane, tert-butanol, tetrahydrofuran, toluene, benzene and/or mixtures of these solvents. The reaction is completed after several hours. It is recommended to control the reaction by thin-layer chromatography. The reaction mixture is worked up after the starting material has been converted as usual, for example by precipitation, extraction, recrystallization and/or column chromatography.

The starting materials of Formula II are all known or readily preparable using fully conventional methods starting with known compounds.

Starting materials and methods for their preparation are described in U.S. Pat. No. 4,129,564.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

7α-Acetylthio-15β,16β-methylene-3-oxo-17α-pregna-1,4-diene-21,17-carbolactone 1.5 g of 7α-acetylthio-15β,16β-methylene-3-oxo-17α-pregn-4-ene-21,17-carbolatone is boiled for 24 hours with 50 ml of benzene and 1.5 g of 2,3-dichloro-5,6-dicyano-p-benzoquinone. The reaction solution is diluted with ether, washed with sodium bicarbonate solution and water, dried, and evaporated. The residue is purified by column chromatography on silica gel, thus obtaining 820 mg of 7α-acetylthio-15β,16β-methylene-3-oxo-17α-pregna-1,4-diene-21,17-carbolactone, mp 269.6° C.

After further recrystallization and chromatography, the compound melts at 277.7° C.

| λ [nm] | 589 | 578 | 546 | 436 | 365 | in CHCl$_3$ |
|---|---|---|---|---|---|---|
| [α] [°] | −86.2 | −91.2 | −105.8 | −217 | −452.4 | |

EXAMPLE 2

7α-Acetylthio-15α,16α-methylene-3-oxo-17α-pregna-1,4-diene-21,17-carbolactone 350 mg of 7α-acetylthio-15α,16α-methylene-3-oxo-17α-pregn-4-ene-21,17-carbolactone is agitated in 7 ml of toluene with 350 mg of 2,3-dichloro-5,6-dicyano-p-benzoquinone for 24 hours at 80° C. The reaction solution is diluted with ether, washed with sodium bicarbonate solution and water, dried, and evaporated. The residue is chromatographed on silica gel, thus obtaining 240 mg of 7α-acetylthio-15α,16α-methylene-3-oxo-17α-pregna-1,4-diene-21,17-carbolactone as an oil.

UV: $\epsilon_{241}=17,800$ $[\alpha]_D^{23} = -26.8°$ in chloroform.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 7α-acylthio-15,16-methylene-3-oxo-17α-pregna-1,4-diene-21,17-carbolactone of the formula

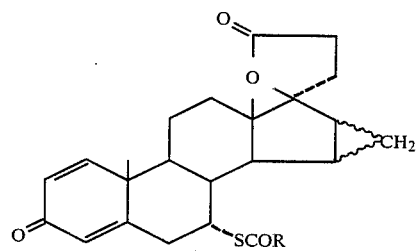

wherein
the 15,16-methylene group can be in the α- or β-configuration, and
R is C$_{1-5}$-alkyl.

2. 7α-acetylthio-15β,16β-methylene-3-oxo-17α-pregna-1,4-diene-21,17-carbolactone, a compound of claim 1.

3. 7α-acetylthio-15α,16α-methylene-3-oxo-17α-pregna-1,4-diene-21,17-carbolactone, a compound of claim 1.

4. A compound of claim 1 wherein the 15,16-methylene group is in the α-configuration.

5. A compound of claim 1 wherein the 15,16-methylene group is in the β-configuration.

6. A compound of claim 1 wherein R is methyl, ethyl or propyl.

7. A pharmaceutical composition containing an amount of a compound of claim 1 effective as an antialdosterone agent and a pharmacologically acceptable carrier.

8. A pharmaceutical composition of claim 7 containing two of said compounds.

9. A pharmaceutical composition of claim 1 wherein the amount of said compound is 10–100 mg.

10. A pharmaceutical composition of claim 7 adapted for oral administration.

11. A method of achieving an antialdosterone effect in a patient in need of such treatment comprising administering an amount of a compound of claim 1 effective as an antialdosterone agent.

12. A method of achieving a diuretic effect in a patient in need of such treatment comprising administering to the patient a diuretically effective amount of a compound of claim 1.

* * * * *